(12) United States Patent
Bresler et al.

(10) Patent No.: US 7,553,998 B2
(45) Date of Patent: Jun. 30, 2009

(54) ENERGY-EFFICIENT PROCESS FOR PARA-XYLENE PRODUCTION

(75) Inventors: Leo Bresler, Northbrook, IL (US); Robert B. Larson, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 478 days.

(21) Appl. No.: 11/425,531

(22) Filed: Jun. 21, 2006

(65) Prior Publication Data

US 2007/0299289 A1    Dec. 27, 2007

(51) Int. Cl.
*C07C 5/27* (2006.01)
*C07C 4/12* (2006.01)

(52) U.S. Cl. .................. 585/319; 585/470; 585/488; 585/480; 585/481

(58) Field of Classification Search .................. 585/319, 585/470, 488, 480, 481
See application file for complete search history.

(56) References Cited

U.S. PATENT DOCUMENTS

| | | | |
|---|---|---|---|
| 3,856,872 A | 12/1974 | Morrison | 260/668 A |
| 3,948,758 A | 4/1976 | Bonacci et al. | 208/92 |
| 4,211,886 A * | 7/1980 | Tabak et al. | 585/321 |
| 4,899,011 A | 2/1990 | Chu et al. | 585/481 |
| 5,977,420 A | 11/1999 | Abichandani et al. | 585/319 |
| 6,222,086 B1 | 4/2001 | Sharma et al. | 585/481 |
| 6,448,459 B1 | 9/2002 | Magne-Drisch et al. | 585/478 |
| 6,660,896 B1 | 12/2003 | Buchanan et al. | 585/481 |

* cited by examiner

*Primary Examiner*—Thuan Dinh Dang
(74) *Attorney, Agent, or Firm*—Maryann Maas (57) ABSTRACT

This invention is drawn to a process for producing and recovering one or more high-purity xylene isomers from a feed stream having a substantial content of $C_9$ and heavier hydrocarbons. The feed stream is processed to de-ethylate heavy aromatics, fractionated and passed to a circuit comprising $C_8$-aromatic isomer recovery and isomerization to recover the high-purity xylene isomer with lowered energy costs.

6 Claims, 4 Drawing Sheets

ENERGY-EFFICIENT PROCESS FOR PARA-XYLENE PRODUCTION

FIELD OF THE INVENTION

This invention relates to catalytic hydrocarbon conversion, and more specifically to aromatics isomerization.

BACKGROUND OF THE INVENTION

The xylene isomers are important intermediates which find wide and varied application in chemical syntheses. Para-xylene is a feedstock for terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

The proportions of xylene isomers obtained from catalytic reforming or other sources generally do not match demand proportions as chemical intermediates, and further comprise ethylbenzene which is difficult to separate or to convert. Para-xylene in particular is a major chemical intermediate with rapidly growing demand, but amounts to only 20-25% of a typical $C_8$-aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture approaching equilibrium concentrations.

One problem in such a process loop comprising para-xylene recovery and $C_8$-aromatics isomerization is the presence of $C_9$ and heavier aromatics ("$C_9$+aromatics") in the feed stream to the process combination. Generally the presence of substantial $C_9$+aromatics in the isomerization or separation processes is unacceptable or undesirable from the standpoint of process performance or catalyst/adsorbent life. Usually the feed stream is fractionated to remove $C_9$+aromatics before being sent to the process loop, an expensive step since the entire $C_8$-aromatics portion must be lifted overhead as well as achieving the separation between the heaviest $C_8$s and lightest $C_9$+s. Avoidance of the resulting expensive energy and investment costs would be an advantage.

Various catalysts and processes have been developed to effect xylene isomerization, and these usually are differentiated by the manner of processing ethylbenzene associated with the xylene isomers. Ethylbenzene is not easily isomerized to xylenes, and separation from the xylenes by superfractionation or adsorption is very expensive. Isomerization of a mixture of xylenes and ethylbenzene followed by recovery of para-xylene and recycle of the resulting $C_8$-aromatic raffinate thus tends to result in a buildup of the ethylbenzene concentration in the recycle. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. Some combination of these approaches can be found in the art.

Processes have been disclosed during the past quarter-century or so using one or more molecular-sieve catalysts for xylene isomerization. For example, U.S. Pat. No. 3,856,872 (Morrison) teaches xylene isomerization and ethylbenzene conversion with a catalyst comprising ZSM-5, -12, or -21 zeolite. U.S. Pat. No. 3,948,758 (Bonacci et al.) discloses the processing of an aromatics-rich reformate stream by hydrocracking, fractionation to separate benzene, toluene and $C_9$+aromatics, separation of a desired isomer from the $C_8$ aromatics and isomerization of the hydrocarbons lean in the desired isomer. U.S. Pat. No. 4,899,011 (Chu et al.) teaches isomerization of $C_8$ aromatics using two zeolites, each of which is associated with a strong hydrogenation metal. U.S. Pat. No. 5,977,420 (Abichandani et al.) discloses a processing scheme in which a $C_8$+feed is subjected to ethylbenzene conversion followed by fractionation to remove $C_9$+, with the overhead processed in a loop comprising a benzene/toluene column, para-xylene recovery, and isomerization with the isomerate returned to the benzene/toluene column. U.S. Pat. No. 6,222,086 (Sharma et al.) teaches the use of two zeolitic catalysts for the isomerization of a mixture of xylenes and ethylbenzene wherein the content of platinum-group metal in the second catalyst is no more than about 30% of that in the first catalyst. U.S. Pat. No. 6,448,459 (Magne-Drisch et al.) discloses a process combination comprising recovery and isomerization of a first fraction of enriched ethylbenzene concentrate, recovery of para-xylene by adsorption from the second fraction from ethylbenzene enrichment, and isomerization of raffinate and desorbent from the para-xylene adsorption step. U.S. Pat. No. 6,660,896 (Buchanan et al.) teaches a process for isomerizing a feed containing ethylbenzene and a mixture of xylene isomers using first and second catalysts in the presence of hydrogen to produce a product having higher-than equilibrium para-xylene. Although these references teach individual elements of the present invention, none of the art suggests combination of the elements to obtain the critical features of the process of the present invention.

None of the art suggests the present efficient process and catalyst combination for obtaining paraxylene from a $C_8$+feedstock having a substantial content of $C_9$+aromatics.

SUMMARY OF THE INVENTION

A principal object of the present invention is to provide a novel process using a combination of catalysts and systems tailored to specific reactions for isomerization of $C_8$-aromatic hydrocarbons to obtain improved yields of desired xylene isomers with low cyclic losses and recycle rate when processing a feed stream having a substantial concentration of $C_9$+aromatics.

This invention is based on the discovery that a process comprising a combination of a vapor-phase zone for converting $C_9$+aromatics followed by fractionation to remove light and heavy ends to provide an intermediate stream for a system comprising para-xylene recovery and a zone for the isomerization of para-depleted xylenes yields para-xylene with reduced energy costs.

A broad embodiment of the invention is a process for the production and recovery of one or more high-purity xylene isomers from a feed stream comprising alkylaromatic hydrocarbons and containing about 1.0 wt.-% or more of $C_9$ and heavier hydrocarbons including about 0.5 wt.-% or more of methylethylbenzenes, comprising the sequential steps of contacting the feed stream in the presence of hydrogen with a heavy-aromatics-conversion catalyst to obtain a de-ethylated aromatic stream having a lower content of ethylaromatic hydrocarbons than the content in the feed stream, fractionating the de-ethylated aromatic stream to separate a light product comprising $C_7$ and lighter hydrocarbons and a heavy product comprising $C_9$ and heavier hydrocarbons from a intermediate stream comprising $C_8$ aromatics, subjecting at least a portion of the intermediate stream, along with an isomerized stream, to an isomer-recovery process to recover at least one high-purity xylene isomer and yield a $C_8$-aromatic raffinate stream comprising non-recovered $C_8$-aromatic isomers; and contacting at least a portion of the $C_8$-aromatic raffinate stream with an isomerization catalyst in an isomerization zone to obtain the isomerized stream comprising a concentration of at least one xylene isomer that is higher than the concentration in the $C_8$-aromatic raffinate stream.

A more specific embodiment of the invention is a process for the production and recovery of one or more high-purity xylene isomers from a feed stream comprising alkylaromatic hydrocarbons and containing about 1.0 wt.-% or more of $C_9$ and heavier hydrocarbons including about 0.5 wt.-% or more of methylethylbenzenes, comprising the sequential steps of contacting the feed stream in the presence of hydrogen with a heavy-aromatics-conversion catalyst to obtain a de-ethylated aromatic stream having a lower content of methylethylbenzenes than the content in the feed stream, fractionating the de-ethylated aromatic stream to separate a light product comprising $C_7$ and lighter hydrocarbons and a heavy product comprising $C_9$ and heavier hydrocarbons from a intermediate stream comprising $C_8$ aromatics, subjecting at least a portion of the intermediate stream, along with an isomerized stream, to an isomer-recovery process to recover at least one high-purity xylene isomer and yield a $C_8$-aromatic raffinate stream comprising non-recovered $C_8$-aromatic isomers; and contacting at least a portion of the $C_8$-aromatic raffinate stream with an isomerization catalyst in an isomerization zone at isomerization conditions in the presence of minimal hydrogen to obtain the isomerized stream comprising a concentration of at least one xylene isomer that is higher than the concentration in the $C_8$-aromatic raffinate stream.

A yet more specific embodiment is a process for the production and recovery of one or more high-purity xylene isomers from a catalytic reformate, comprising the sequential steps of fractionating the catalytic reformate to obtain a light reformate and a heavy-reformate feed stream containing about 1.0 wt.-% or more of $C_9$ and heavier hydrocarbons including about 0.5 wt.-% or more of methylethylbenzenes, comprising the sequential steps of contacting the feed stream in the presence of hydrogen with a heavy-aromatics-conversion catalyst to obtain a de-ethylated aromatic stream having a lower content of ethylaromatic hydrocarbons than the content in the feed stream, fractionating the de-ethylated aromatic stream to separate a light product comprising $C_7$ and lighter hydrocarbons and a heavy product comprising $C_9$ and heavier hydrocarbons from a intermediate stream comprising $C_8$ aromatics, subjecting the light reformate stream to an aromatics-extraction and fractionation step to separate benzene, toluene and a toluene-bottoms stream from a non-aromatic raffinate, contacting the heavy product comprising $C_9$ and heavier hydrocarbons and at least a portion of the toluene in a transalkylation zone with a transalkylation catalyst at transalkylation conditions to obtain a transalkylation product, fractionating the transalkylation product to separate a $C_7$ and lighter stream, an intermediate stream comprising $C_8$ aromatics and a $C_9$ and heavier stream, subjecting at least a portion of the intermediate stream, along with an isomerized stream, to an isomer-recovery process to recover at least one high-purity xylene isomer and yield a $C_8$-aromatic raffinate stream comprising non-recovered $C_8$-aromatic isomers, and contacting at least a portion of the $C_8$-aromatic raffinate stream with an isomerization catalyst in an isomerization zone in liquid phase at isomerization conditions in the substantial absence of hydrogen to obtain the isomerized stream comprising a concentration of at least one xylene isomer that is higher than the concentration in the $C_8$-aromatic raffinate stream.

These as well as other objects and embodiments will become evident from the following detailed description of the invention.

DETAILED DESCRIPTION OF THE INVENTION

The non-equilibrium alkylaromatic feed stream to aromatics isomerization comprises isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination suitable for isomerization to obtain at least one more valuable alkylaromatic isomer in an isomerized product. The feed stream comprises one or more ethylaromatic hydrocarbons containing at least one ethyl group, i.e., at least one R of at least one of the alkylaromatic hydrocarbons is $C_2H_5$. Suitable components of the feed stream generally include, for example but without so limiting the invention, ethylbenzene, meta-xylene, ortho-xylene, para-xylene, ethyltoluenes, trimethylbenzenes, diethyl-benzenes, triethylbenzenes, propylbenzenes, methylpropylbenzenes, ethylpropylbenzenes, diisopropylbenzenes, and mixtures thereof. The present invention is characterized by a feed stream having a substantial content, about 1.0 wt-% or more, and preferably at least about 5 wt-%, of $C_9$ and heavier hydrocarbons. The invention is demonstrated by performance with a feed stream containing about 0.5 wt-% or more and preferably at least about 2 wt-% of methylethylbenzenes.

A non-equilibrium $C_8$-aromatic feed stream comprising xylenes and ethylbenzene generally will have an ethylbenzene content in the approximate range of 1 to 50 wt-%, an ortho-xylene content in the approximate range of 0 to 35 wt-%, a meta-xylene content in the approximate range of 20 to 95 wt-% and a para-xylene content in the approximate range of 0 to 30 wt-%. By "non-equilibrium" is meant that at least one $C_8$-aromatic isomer is present in a concentration that differs substantially from the equilibrium concentration at isomerization conditions.

The alkylaromatic feed stream may be derived from any of a variety of original sources, e.g., petroleum refining, thermal or catalytic cracking of hydrocarbons, coking of coal, or petrochemical conversions. Preferably the feed stream utilized in the present invention is found in appropriate fractions from various petroleum-refinery streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 wt-%. Preferably the isomerizable hydrocarbons consist essentially of aromatics, however, to ensure pure products from downstream recovery processes.

Figure 1:
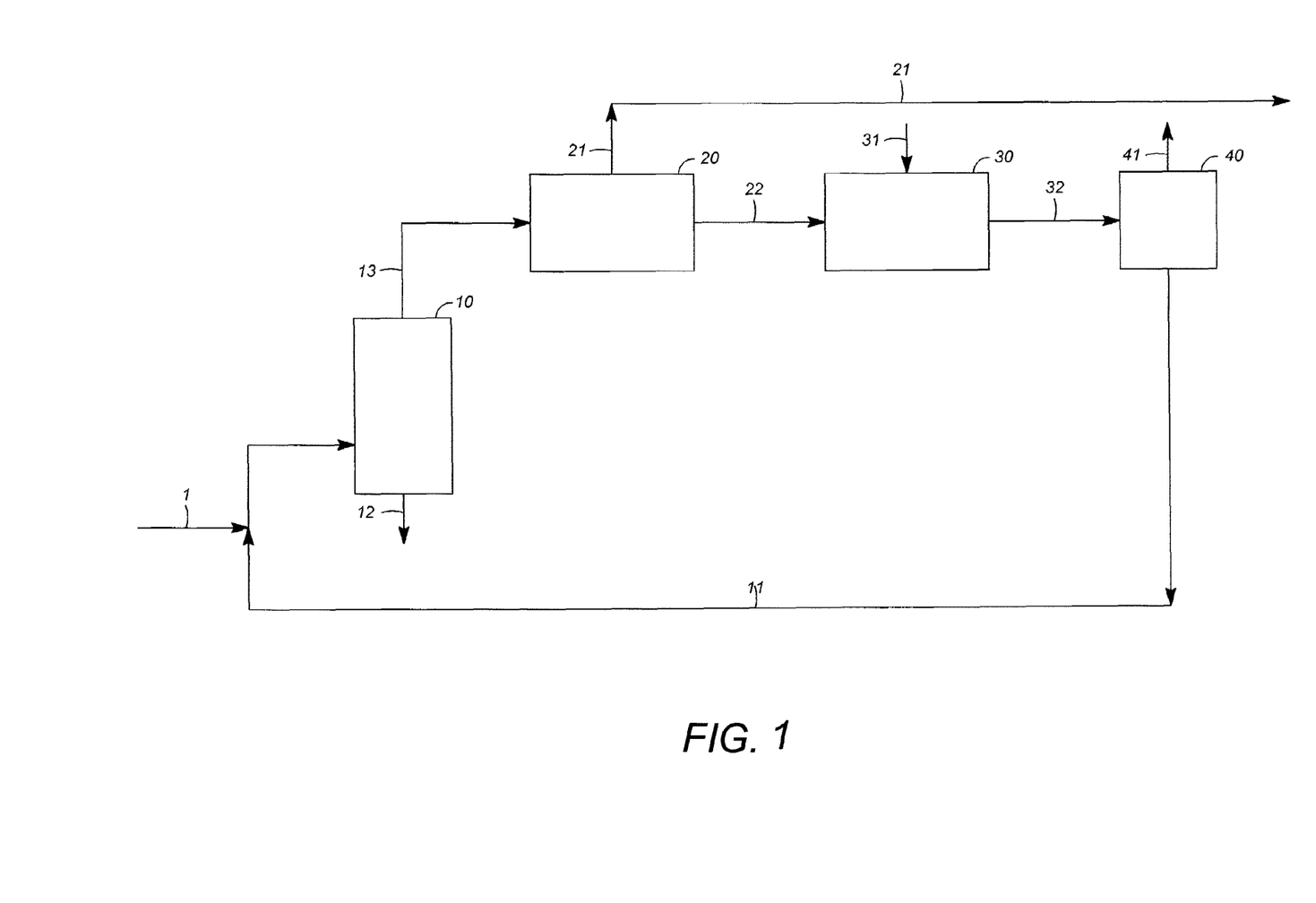
FIG. 1 illustrates $C_8$-aromatics processing according to the known art.

Processing of $C_8$ aromatics to produce para-xylene according to the known art usually would proceed as shown in FIG. 1. The feed stream 1 comprises $C_8$ and heavier aromatics, which is processed along with a recycle stream 11 in fractionator 10 to remove $C_9$ and heavier aromatics in stream 12. The $C_9$ and heavier aromatics could have an adverse effect on downstream separation step 20 and isomerization 30 if not removed from the feed stream by fractionation.

The fractionator thus yields a $C_8$-aromatics stream 13 which passes to separation step 20. This stream usually is processed to selectively recover the para-xylene isomer by one or both of selective adsorption or crystallization. The pure para-xylene is recovered as a product in stream 21, with the balance of $C_8$ aromatics passing to isomerization unit 30. Optionally in the presence of hydrogen in stream 31, the isomerization unit establishes a near-equilibrium balance of xylene isomers in stream 32 using one or more of a variety of catalysts which also may convert ethylbenzene as discussed earlier. The isomerization product passes to detoluenizer column 40 which removes $C_7$ and lighter materials in 41 to yield recycle stream 11 to fractionator 10.

Figure 2:
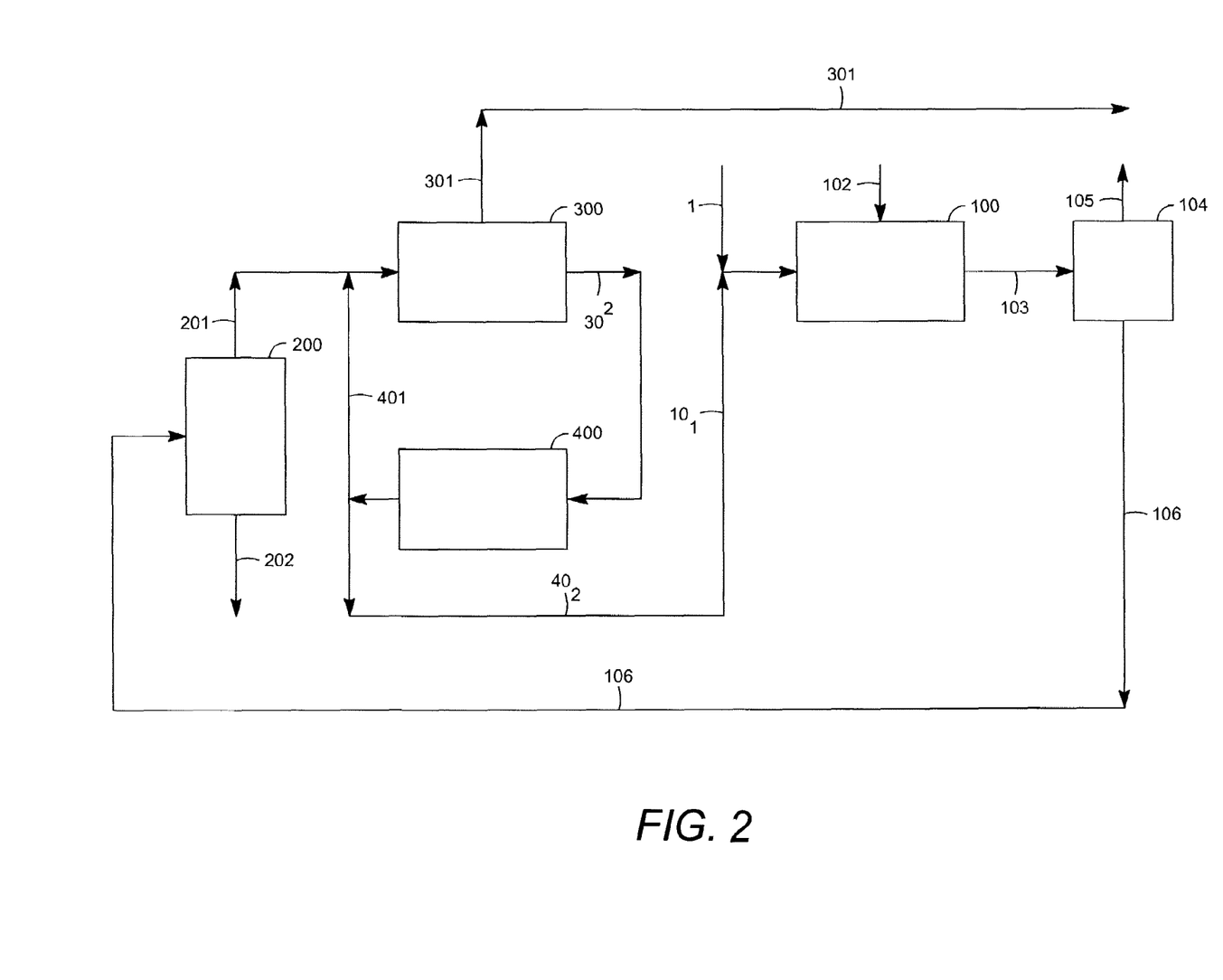
FIG. 2 illustrates $C_8$-aromatics processing according to an embodiment of the invention.

FIG. 2 illustrates an embodiment of the invention. This scheme illustrates the use of the features of two different isomerization techniques to substantially reduce the volume of recycle in the process, concomitantly reducing the substantial size and energy requirement of the large fractionator which separates $C_8$ from $C_9$ aromatics.

In this embodiment, a feed stream 1 comprising $C_8$ and heavier aromatics is processed along with a purge stream 101 in a heavy-aromatics-conversion zone 100. The heavy-aromatics-conversion zone contains a heavy-aromatics-conversion catalyst which is tolerant of a substantial concentration of $C_9$ aromatics in the feed while converting ethylbenzene and methylethylbenzenes. The feed stream contacts the catalyst in the presence of hydrogen supplied in stream 102 at suitable heavy-aromatics-conversion conditions comprising a temperature ranging from about 200° to 600° C. or more, preferably in the range of from about 300° to 500° C. The pressure generally is from about 100 kPa to 5 MPa absolute, preferably from 500 kPa to about 3 MPa. The heavy-aromatics-conversion zone contains a sufficient volume of catalyst to provide a liquid hourly space velocity with respect to the intermediate stream of from about 0.5 to 50 $hr^{-1}$, and preferably 0.5 to 20 $hr^{-1}$. The feed stream optimally is reacted in admixture with hydrogen at a hydrogen/hydrocarbon mole ratio of about 0.5:1 to 25:1; other inert diluents such as nitrogen, argon and light hydrocarbons may be present along with the hydrogen. The heavy-aromatics-conversion zone may comprise a single reactor or two or more separate reactors with suitable means therebetween to ensure that the desired isomerization temperature is maintained at the entrance to each reactor. The reactants may be contacted with the catalyst bed in upward-, downward-, or radial-flow fashion, and the reactants may be in liquid phase, a mixed liquid-vapor phase, or a vapor phase when contacted with the catalyst to obtain an isomerized product.

A heavy-aromatics-conversion catalyst usually comprises a zeolitic component, a metal component and an inorganic oxide. Zeolites favored as components of the heavy-aromatics-conversion catalyst include one or more of ATO, BEA, EUO, FAU, FER, MCM-22, MEL, MFI, MOR, MTT, MTW, NU-87 OFF, Omega, UZM-5, UZM-8 and TON, according to the Atlas of Zeolite Structure Types. Preferred zeolites include one or both of MFI and MOR. The metal component comprises one or more of the base and noble metals in a proportion in the catalyst of from about 0.01 to 10 wt.-%. The one or more metals may be selected from the group consisting of Re, Sn, Ge, Pb, Co, Ni, In, Ga, Zn, U, Dy, Tl, and the platinum-group metals, with rhenium being favored. An inorganic-oxide binder, preferably alumina, comprises the balance of the catalyst. A preferred catalyst shape is a sphere, with an alternative suitable shape being an extrudate.

Effluent from the heavy-aromatics-conversion zone passes as stream 103 to a detoluenizer 104 for the substantial separation overhead of toluene and lighter components in stream 105 from $C_8$ and heavier aromatics. The $C_8$ and heavier aromatics in stream 106 pass to fractionator 200 to separate $C_8$ aromatics in stream 201 from $C_9$ and heavier aromatics in stream 202. Fractionators 104 and 200 are substantially smaller than the corresponding columns in the FIG. 1 control scheme, as the present purge stream 101 is substantially smaller than the FIG. 1 recycle stream 11 and the circulation of material through the first-isomerization/fractionation loop is substantially less than in the control. This is particularly important with respect to the fractionator 200, as this fractionator generally represents an important portion of the capital and energy costs of such complexes for the production and recovery of individual $C_8$-aromatic isomers.

Overhead 201 joins a recycle stream 401 as feed to $C_8$-aromatic-isomer recovery unit 300. The process employed to recover a particular isomer product from the isomerized product is not deemed to be critical to the instant invention, and any effective recovery scheme known in the art may be used. $C_8$ aromatics usually are processed to selectively recover the para-xylene isomer, although other isomers may be recovered instead or in addition. Para-xylene usually is recovered by either or a combination of adsorption and crystallization. Selective adsorption is preferred using crystalline aluminosilicates according to U.S. Pat. No. 3,201,491. Improvements and alternatives within the preferred adsorption recovery process are described in, for example, U.S. Pat. Nos. 3,626,020; 3,696,107; 4,039,599; 4,184,943; 4,381,419 and 4,402,832, incorporated herein by reference thereto. The desired $C_8$-aromatic isomer is recovered as stream 301, with $C_8$-aromatic raffinate comprising undesired isomers passing as stream 302 to isomerization unit 400.

Unit 400 comprises isomerization targeted specifically to the isomerization of xylenes in the feedstock to a near-equilibrium mixture with minimal conversion to lighter and heavier products. The $C_8$-aromatic stream 302, a non-equilibrium mixture of $C_8$-aromatic isomers, contacts an isomerization catalyst in at suitable second-isomerization conditions. Such conditions comprise temperature ranging from about 100° to about 500° C., and preferably from about 200° to 400° C. The pressure is from about 500 kPa to 5 MPa absolute. The isomerization unit contains a sufficient volume of catalyst to provide a liquid hourly space velocity with respect to the feed stream of from about 0.5 to 50 $hr^{-1}$, and preferably 0.5 to 20 $hr^{-1}$. Hydrogen may be present in an amount up to about 15 moles/mole of feed. Preferably the isomerization is carried out in the presence of minimal hydrogen, i.e., the amount of hydrogen present is less than about 0.2 moles/mole of feed. More preferably, the isomerization is carried out in the substantial absence of hydrogen and in the liquid phase with no free hydrogen being added to the feed stream; in this event, any dissolved hydrogen from prior processing is substantially less than 0.05 moles/mole of feed, frequently less than 0.01 moles/mole, and possibly not detectable by usual analytical means. The isomerization zone may comprise a single reactor or two or more separate reactors with suitable means therebetween to ensure that the desired isomerization temperature is maintained at the entrance to each reactor. The reactants may be contacted with the catalyst bed in upward-, downward-, or radial-flow fashion.

The isomerization catalyst favorably comprises a zeolitic aluminosilicate selected from those which have a $Si:Al_2$ ratio greater than about 10, preferably greater than 20, and a pore diameter of about 5 to 8 angstroms (Å). Specific examples of suitable zeolites are the MFI, MEL, EUO, FER, MFS, MTT, MTW, TON, MOR and FAU types of zeolites. A particularly favored MFI-type zeolite is gallium-MFI, with gallium as a component of the crystal structure. A preferred Ga-MFI has a $Si/Ga_2$ mole ratio of less than 500, and preferably less than 100; the aluminum content concomitantly is very low, with an $Si/Al_2$ mole ratio of greater than 500 and preferably greater than 1000. The proportion of zeolite in the catalyst generally is in the range of from about 1 to 99 wt.-%, and preferably from about 25 to about 75 wt.-%. The isomerization catalyst may contain from about 0.01 to 2.0 wt.-% of a platinum-group metal, favorably platinum, but preferably has the substantial absence of a metallic compound. An inorganic-oxide binder, preferably alumina, comprises the balance of the catalyst. A preferred catalyst shape is a sphere, with an alternative suitable shape being an extrudate.

The isomerized product from the isomerization unit is split into stream 401 recycle to isomer-recovery unit 300 and a smaller purge stream 402. The latter is sent to heavy-aromatics-conversion zone 100 to convert and remove small concentrations of ethylbenzene and lighter and heavier components produced in the isomerization unit in order to prevent the buildup of these components in stream 401.

The process of the invention is usefully applied in the context of an aromatics complex, which utilizes a combination of processes to produce and recover desired aromatic products from naphtha, liquefied petroleum gases, olefin-plant byproducts and other hydrocarbon feedstocks. Such a complex may include, without limiting the invention, feed treating, catalytic reforming or other aromatization, extraction for recovery of aromatics, hydrodealkylation, disproportionation and/or transalkylation.

Figure 3:
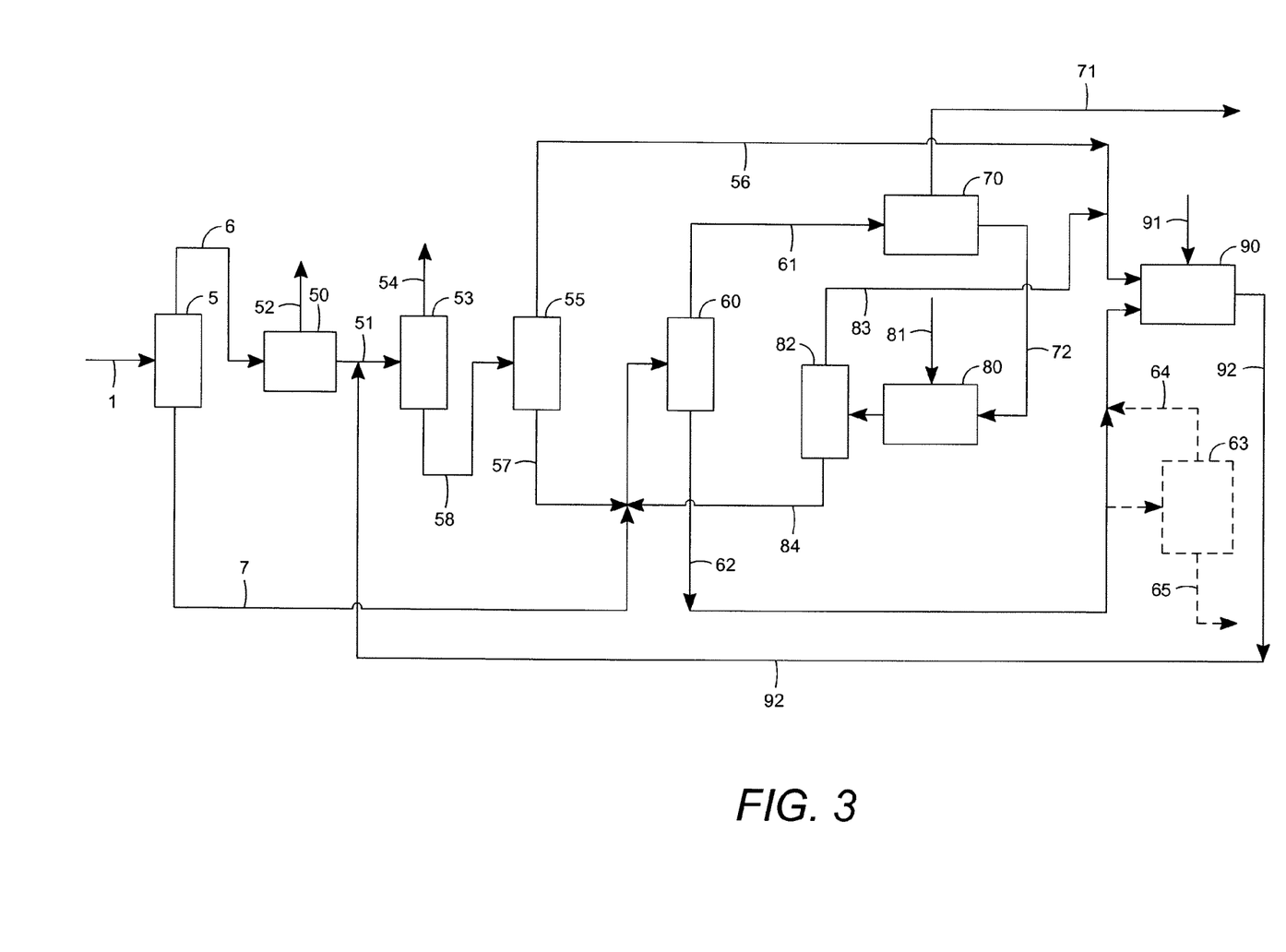
FIG. 3 illustrates a pertinent portion of an aromatics complex of the known art.
Figure 4:
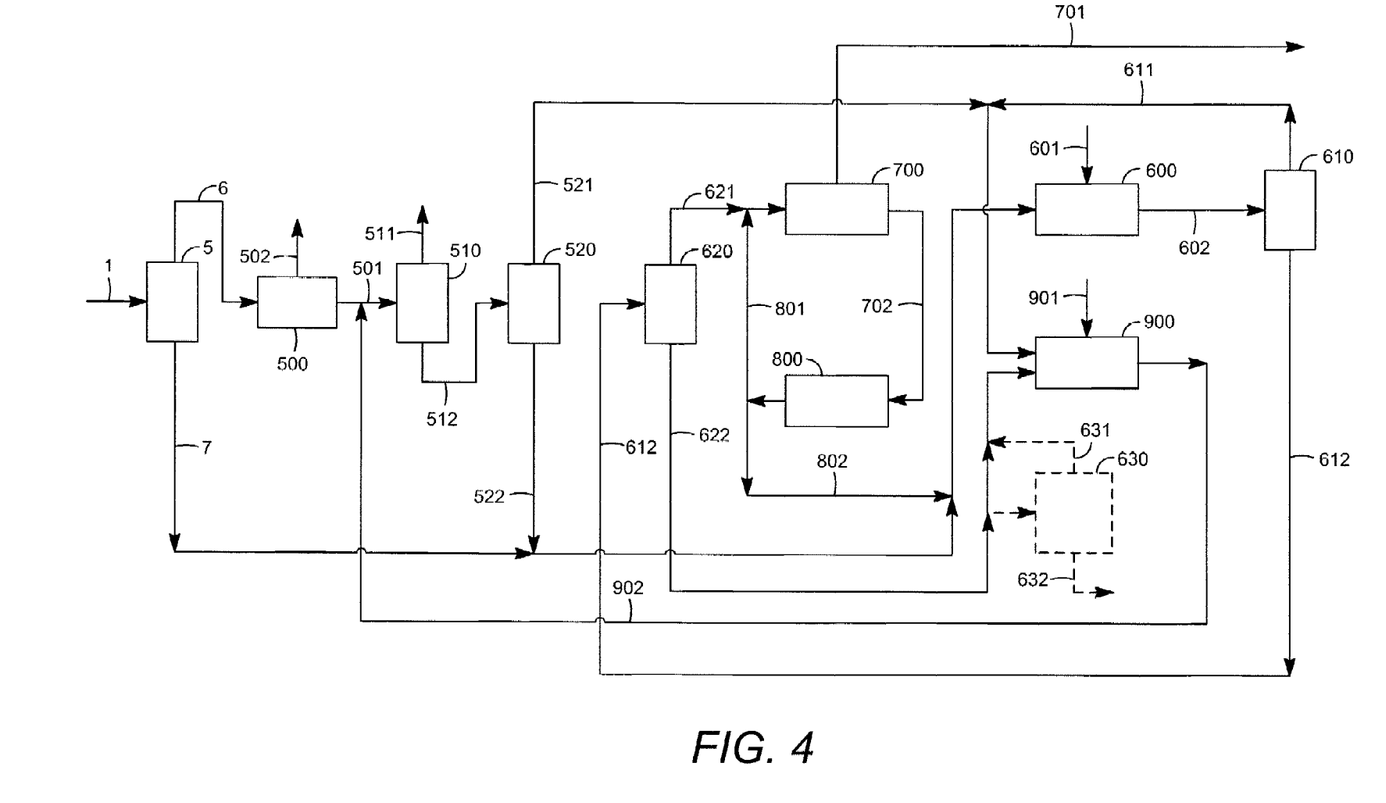
FIG. 4 illustrates a pertinent portion of an aromatics complex based on the present invention.

Examples of such complexes without and with the present invention are illustrated in FIGS. 3 and 4 respectively. FIG. 3 illustrates a pertinent portion of a conventional aromatics complex of the known art. This example is based upon the processing of a catalytic reformats derived from the reforming of naphtha including hydrocarbons in the "BTX" (benzene-toluene-xylenes) range. The catalytic reformate 1 is fractionated in splitter 5 to obtain a light reformate comprising benzene and toluene as stream 6 and a heavy reformate comprising $C_8$ aromatics and in stream 7. The light reformate is processed in an aromatics-extraction step 50 to separate aromatics in stream 51 from a non-aromatic raffinate in stream 52. The aromatics stream is fractionated in steps 53 and 55 to separate benzene in stream 54 and toluene in stream 56 from a bottoms stream 57.

The heavy-reformate stream 7 and bottoms stream 57 are fractionated in unit 60 to separate $C_8$ aromatics 61 from $C_9$ and heavier hydrocarbons 62. The $C_8$ aromatics are subjected to an isomer-recovery process 70 to recover at least one high-purity xylene isomer 71 and yield a $C_8$-aromatic raffinate stream 72 comprising non-recovered $C_8$-aromatic isomers. The $C_8$-aromatic raffinate stream is processed in an isomerization zone 80 in the presence of hydrogen supplied in stream 81 followed by fractionation 82 to separate C7 and lighter in stream 83 from isomerized product 84 isomerized stream comprising a concentration of the xylene isomer in 71 that is higher than the concentration in the $C_8$-aromatic raffinate stream. The isomerized product is fractionated in 60, along with streams 7 and 57, to separate $C_9$ and heavier hydrocarbons 62 from the $C_8$ aromatics 61 which are sent to recovery unit 70. It should be noted that the entire recycle stream to the recovery unit is processed through fractionators 60 and 82.

The $C_9$ and heavier hydrocarbons 62 are optionally or partially processed in fractionator 63 to separate $C_9$ aromatics 64 from $C_{10}$ and heavier hydrocarbons 65. Streams 62 and/or 64 are processed, along with toluene in streams 56 and 83, in a transalkylation zone 90 in the presence of hydrogen in stream 91 to obtain a transalkylation product 92 having an increased concentration of $C_8$ aromatics. The transalkylation product is processed in fractionators 53, 55 and 60 along with the aromatics recovered from catalytic reformate, to separate benzene, toluene and $C_8$ aromatics from heavier hydrocarbons.

FIG. 4 illustrates an aromatics complex based on the present invention with the same feedstock and objectives of the complex of FIG. 3. The first portion of each complex uses identical concepts. Catalytic reformate 1 is fractionated in splitter 5 to obtain a light reformate comprising benzene and toluene as stream 6 and a heavy reformate comprising $C_8$ aromatics and in stream 7. The light reformate is processed in an aromatics-extraction step 500 to separate aromatics in stream 501 from a non-aromatic raffinate in stream 502. Any suitable process for separating high-purity aromatics from non-aromatics may be employed, an example being the liquid-liquid extraction process using sulfolane described in, e.g., U.S. Pat. No. 3,361,664. The aromatics stream is fractionated in steps 510 and 520 to separate benzene in stream 511 and toluene in stream 521 from a bottoms stream 522.

The heavy reformate comprises alkylaromatic hydrocarbons and contains about 1.0 wt.-% or more of $C_9$ and heavier hydrocarbons including about 0.5 wt.-% or more of methylethylbenzenes and is the principal feed stream to the heavy-aromatics-conversion zone 600. The characteristics, conditions and catalyst for this zone are as described above in connection with FIG. 2. The heavy aromatics are converted in the presence of hydrogen 601 to obtain a de-ethylated stream 602 having a lower content of ethylaromatic hydrocarbons than the content in the feed stream. The de-ethylated aromatic stream is fractionated in unit 610 to separate a light product comprising $C_7$ and lighter hydrocarbons in stream 611 from $C_8$ and heavier in stream 612, and in fractionator 620 to separate an intermediate stream 621 comprising $C_8$ aromatics from a heavy product comprising $C_9$ and heavier hydrocarbons in stream 622.

Overhead 621 joins a recycle stream 801 as feed to $C_8$-aromatic-isomer recovery unit 700. The process employed to recover a particular isomer product 701 from the isomerized product is not deemed to be critical to the instant invention, and any effective recovery scheme known in the art may be used. $C_8$ aromatics usually are processed to selectively recover the para-xylene isomer, although other isomers may be recovered instead or in addition. Para-xylene usually is recovered by either or a combination of adsorption and crystallization. Selective adsorption is preferred as described for the corresponding unit in FIG. 2. $C_8$-aromatic raffinate comprising undesired isomers passes as stream 702 to isomerization unit 800.

Unit 800 comprises isomerization targeted specifically to the isomerization of xylenes in the feedstock to a near-equilibrium mixture with minimal conversion to lighter and heavier products. The $C_8$-aromatic stream 702, a non-equilibrium mixture of $C_8$-aromatic isomers, contacts an isomerization catalyst at suitable isomerization conditions. This unit yields only a small amount of non-$C_8$ byproducts, and most of the product can be recycled directly to the isomer-recovery unit in stream 801. A smaller purge portion of the product is sent as stream 802 to heavy-aromatics-conversion zone 600 to convert and remove small concentrations of ethylbenzene and lighter and heavier components produced in the isomerization unit in order to prevent the buildup of these components in stream 801. Preferably the isomerization is performed in the presence of minimal hydrogen, and especially in the substantial absence of hydrogen. Isomerization conditions and catalysts are as described for the FIG. 2 unit 500.

The $C_9$ and heavier hydrocarbons 622 are optionally or partially processed in fractionator or 630 to separate $C_9$ aromatics 631 from $C_{10}$ and heavier hydrocarbons 632. Streams 622 and/or 631 are processed, along with toluene in streams 521 and 611, in a transalkylation zone 900 in the presence of hydrogen in stream 901 to obtain a transalkylation product 902 having an increased concentration of $C_8$ aromatics. The transalkylation product is processed in fractionators 510 and 520 and through unit 600 and subsequent fractionation, along with the aromatics recovered from catalytic reformate, to separate benzene, toluene and $C_8$ aromatics from heavier hydrocarbons.

The transalkylation feed may contact a transalkylation catalyst in upward-, downward-, or radial-flow fashion, and the reactants may be in liquid phase, mixed liquid-vapor phase, or vapor phase. A favored catalyst comprises a zeolite component, a metal component and an inorganic oxide. Suitable zeolites include one or more of ATO, BEA, EUO, FAU, FER, MCM-22, MEL, MFI, MOR, MTT, MTW, NU-87 OFF, Omega, UZM-5, UZM-8 and TON, according to the IUPAC Atlas of Zeolite Structure Types; a particularly favored zeolitic molecular-sieve component is mordenite. The proportion of zeolite in the catalyst generally is in the range of from about 1 to 99 wt.-%, and preferably from about 25 to about 75 wt.-%. The metal component comprises one or more of the base and noble metals in a proportion in the catalyst of from about 0.01 to 10 wt.-%. The one or more metals may be selected from the group consisting of Re, Sn, Ge, Pb, Co, Ni, In, Ga, Zn, U, Dy, Tl, and the platinum-group metals, with rhenium being favored. The inorganic-oxide binder, preferably alumina, comprises the balance of the catalyst. A preferred catalyst shape is an extrudate, with an alternative suitable shape being a sphere.

It should be noted that this combination avoids the large recycle of $C_8$ aromatics through the corresponding FIG. 3 fractionators 60 and 82, since the direct recycle through units 700 and 800 of FIG. 4 reduces the duty of fractionators 610 and 620 by a corresponding amount.

The foregoing description and following examples are presented only to illustrate certain specific embodiments of the invention, and should not be construed to limit the scope of the invention as set forth in the claims. There are many possible other variations, as those of ordinary skill in the art will recognize, within the spirit of the invention.

EXAMPLE 1

A conversion test was conducted on a feedstock containing 80 wt.-% $C_8$ aromatics and 20 wt.-% $C_9$ aromatics including 8.5 wt.-% methylethylbenzenes, using a catalyst comprising platinum on aluminum-phosphate-bound MFI at a temperature of 400° C., pressure of 1.3 MPa and hydrogen/hydrocarbon ratio of 4. The conversion of methylethylbenzenes was 70%, and propylbenzenes were not detected in the product.

EXAMPLE 2

A conversion test was conducted on a feedstock comprising 66 wt.-% $C_9$ and $C_{10}$ aromatics including 17.3 wt.-% methylethylbenzenes, using a catalyst comprising rhenium on an alumina-bound mordenite base. Operating conditions comprised an average temperature of 372° C., pressure of 3.7 MPa and molar hydrogen/hydrocarbon ratio of 3.8. Overall conversion of $C_9$ and $C_{10}$ aromatics was 70.5 wt.-% and conversion of methylethylbenzenes was 81.3 wt.-%; propylbenzenes in the product amounted to less than 0.01 wt.-%.

EXAMPLE 3

An engineering study was carried out for the production of para-xylene from heavy reformate, comparing a process of the known art according to FIG. 3 and a process of the invention according to FIG. 4. The basis of the study was the production of 1,600,000 metric tons/annum of para-xylene. Comparative principal yields in thousands of tons/annum and comparative energy requirements were:

|  | FIG. 3 | FIG. 4 |
|---|---|---|
| Reformate feed | 2933 | 3047 |
| Benzene | 429 | 435 |
| Paraffinic raffinate | 412 | 408 |
| Para-xylene | 1600 | 1600 |
| Net fuel consumption, MW | 248 | 82 |
| Electric power, MW | 20.6 | 16.9 |

Capital costs also were considered, with estimated savings of about 7% in overall capital or over 30% in the fractionation section associated with the conversion units.

What is claimed is:

1. A process for the production and recovery of one or more high-purity xylene isomers from a catalytic reformate, comprising the sequential steps of:
   (a) fractionating the catalytic reformate to obtain a light reformate and a heavy-reformate feed stream comprising alkylaromatic hydrocarbons and containing about 1.0 wt.-% or more of $C_9$ and heavier hydrocarbons including about 0.5 wt.-% or more of methylethylbenzenes;
   (b) contacting the feed stream in the presence of hydrogen with a heavy-aromatics-conversion catalyst in a heavy-aromatics-conversion zone at heavy-aromatics-conversion conditions to obtain a de-ethylated stream having a lower content of methylethylbenzenes than the content in the feed stream;
   (c) fractionating the de-ethylated aromatic stream to separate a light product comprising $C_7$ and lighter hydrocarbons and a heavy product comprising $C_9$ and heavier hydrocarbons from a intermediate stream comprising $C_8$ aromatics;
   (d) subjecting the light reformate stream to an aromatics-extraction and fractionation step to separate benzene, toluene and a toluene-bottoms stream from a non-aromatic raffinate;
   (e) contacting the heavy product comprising $C_9$ and heavier hydrocarbons and at least a portion of the toluene in a transalkylation zone with a transalkylation catalyst at transalkylation conditions to obtain a transalkylation product;
   (f) fractionating the transalkylation product to separate a $C_7$ and lighter stream, an intermediate stream and a $C_9$ and heavier stream;
   (g) subjecting at least a portion of the intermediate stream, along with an isomerized stream, to an isomer-recovery process to recover at least one high-purity xylene isomer and yield a $C_8$-aromatic raffinate stream comprising non-recovered $C_8$-aromatic isomers; and, (h) contacting at least a portion of the $C_8$-aromatic raffinate stream with an isomerization catalyst in an isomerization zone at isomerization conditions comprising substantially less than 0.05 moles of hydrogen/mole of feed to obtain the isomerized stream comprising a concentration of at least one xylene isomer that is higher than the concentration in the $C_8$-aromatic raffinate stream.

2. The process of claim 1 further comprising fractionating the $C_9$ and heavier stream to obtain a $C_9$-aromatics stream as additional feed to the transalkylation zone and a $C_{10}$ and heavier stream.

3. The process of claim 1 comprising processing the entire $C_8$-aromatic raffinate stream in the isomerization zone.

4. The process of claim 1 further comprising processing a portion of the $C_8$-aromatic raffinate stream in the heavy-aromatics-conversion zone.

5. The process of claim 1 wherein step (h) comprises contacting at least a portion of the $C_8$-aromatic raffinate stream with an isomerization catalyst in an isomerization zone at isomerization conditions with no free hydrogen being added to the feed stream.

6. The process of claim 1 wherein the isomerization catalyst comprises from about 10 to 99 wt.-% of at least one zeolitic aluminosilicate and an inorganic-oxide binder and has the substantial absence of a platinum-group metal.

* * * * *